United States Patent
Dharshan

(10) Patent No.: US 10,993,895 B2
(45) Date of Patent: May 4, 2021

(54) COMPOSITION OBTAINABLE BY PASSING SINGLET OXYGEN THROUGH EXTRA VIRGIN OLIVE OIL

(71) Applicant: Kayapan Satya Dharshan, Jakarta (ID)

(72) Inventor: Kayapan Satya Dharshan, Jakarta (ID)

(*) Notice: Subject to any disclaimer, the term of this patent is extended or adjusted under 35 U.S.C. 154(b) by 493 days.

(21) Appl. No.: 15/543,301

(22) PCT Filed: Mar. 22, 2017

(86) PCT No.: PCT/IB2017/051644
§ 371 (c)(1),
(2) Date: Jul. 13, 2017

(87) PCT Pub. No.: WO2018/167544
PCT Pub. Date: Sep. 20, 2018

(65) Prior Publication Data
US 2019/0175470 A1 Jun. 13, 2019

(30) Foreign Application Priority Data

Mar. 13, 2017 (IN) .............................. 201741008643

(51) Int. Cl.
| | |
|---|---|
| *A61K 8/37* | (2006.01) |
| *A61K 8/92* | (2006.01) |
| *A61Q 19/00* | (2006.01) |
| *A61Q 5/00* | (2006.01) |
| *A61K 9/00* | (2006.01) |
| *C11C 3/00* | (2006.01) |
| *A61K 31/23* | (2006.01) |

(52) U.S. Cl.
CPC ................ *A61K 8/37* (2013.01); *A61K 8/922* (2013.01); *A61K 9/0014* (2013.01); *A61K 31/23* (2013.01); *A61Q 5/006* (2013.01); *A61Q 19/007* (2013.01); *A61Q 19/008* (2013.01); *C11C 3/006* (2013.01)

(58) Field of Classification Search
None
See application file for complete search history.

(56) References Cited

U.S. PATENT DOCUMENTS

| | | | | |
|---|---|---|---|---|
| 2,072,231 | A | * | 3/1937 | Whitehead ................ D01F 2/28 106/170.22 |
| 2014/0005423 | A1 | * | 1/2014 | Allen ..................... A61K 8/466 554/85 |

FOREIGN PATENT DOCUMENTS

CA  2713830 A1 * 2/2012 ............... A23B 7/04

OTHER PUBLICATIONS

Morales, M.T., et al., Comparative study of virgin olive oil sensory defects, Food Chemistry 91 (2005) pp. 293-301 (Year: 2005).*
Giuliani, A.A., et al., Chlorophyll photosensitized oxidation of virgin olive oil: A comparison between selected unsaturated model esters and real oil samples, Rivista Italiana Delle Sostanze Grasse, Jan. 2015, pp. 25-36. (Year: 2015).*

* cited by examiner

*Primary Examiner* — Dominic Lazaro
(74) *Attorney, Agent, or Firm* — Fresh IP PLC; Clifford D. Hyra; Aubrey Y. Chen

(57) ABSTRACT

The present invention relates to a novel composition and methods of preparation thereof. More specifically, the compositions are useful as personal care products, as wound healing compositions, as a disinfectant and also for nosocomial infections.

7 Claims, 4 Drawing Sheets

101

102

103

104

101
102
103
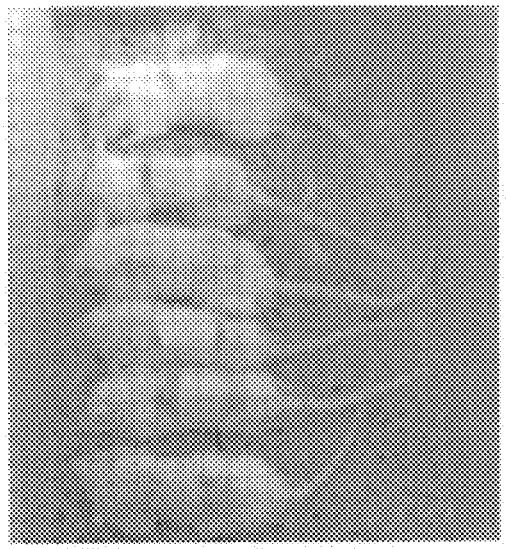
104
Fig: 1

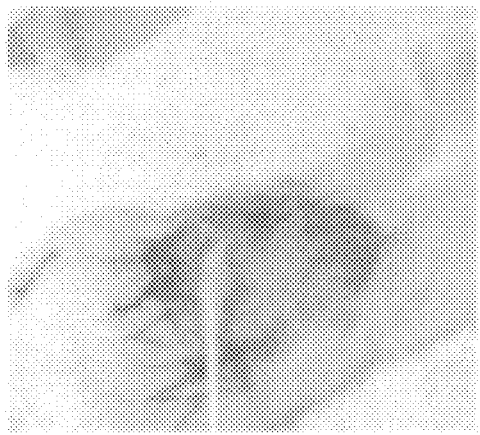
201
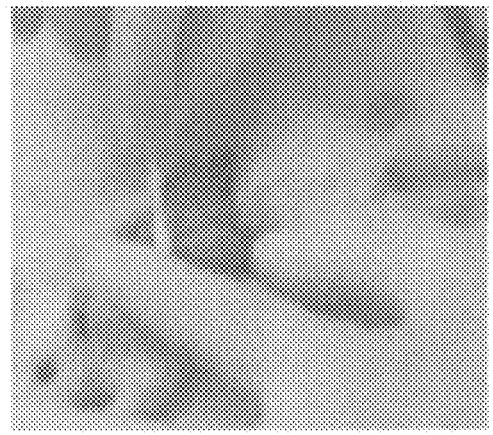
202
203
204
Fig: 2

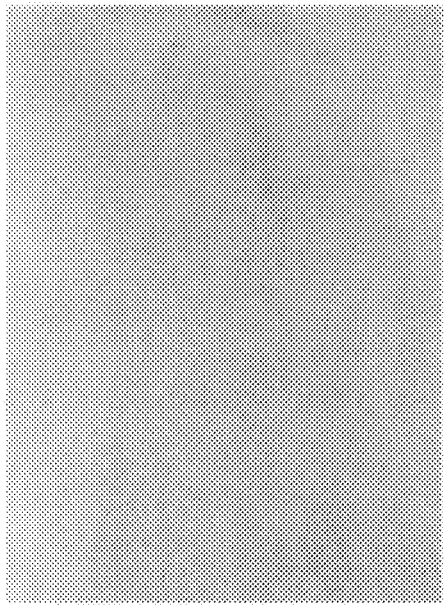 301
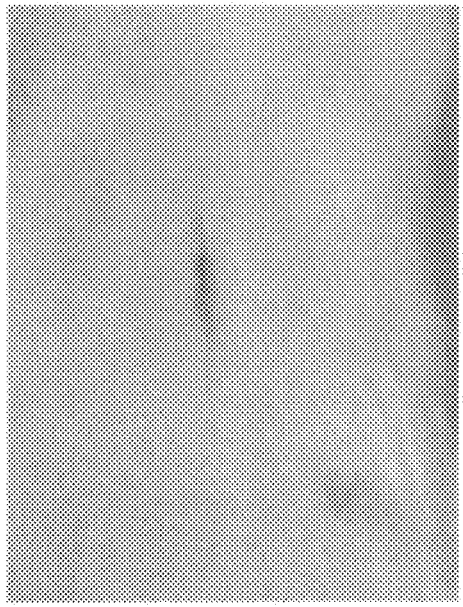 302
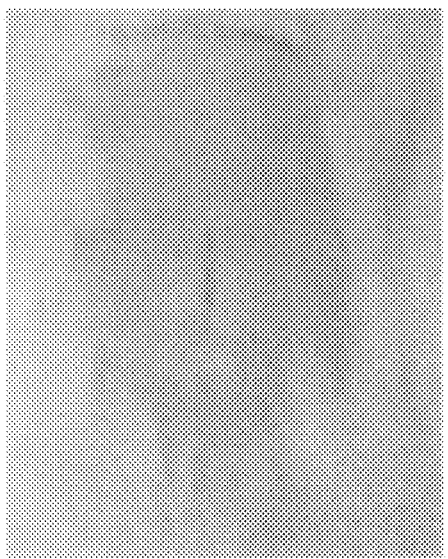 303
 304
Fig: 3

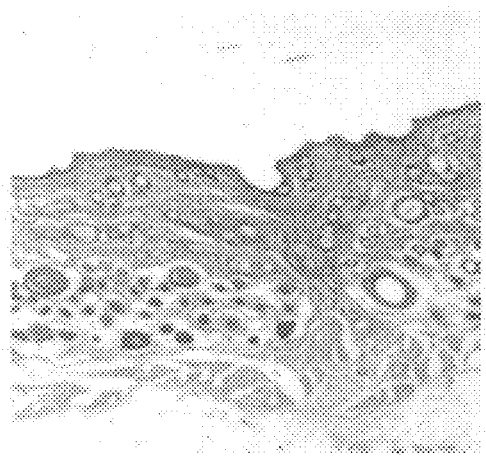
101
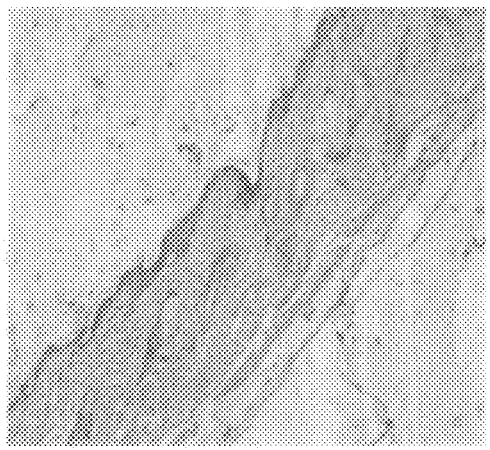
102
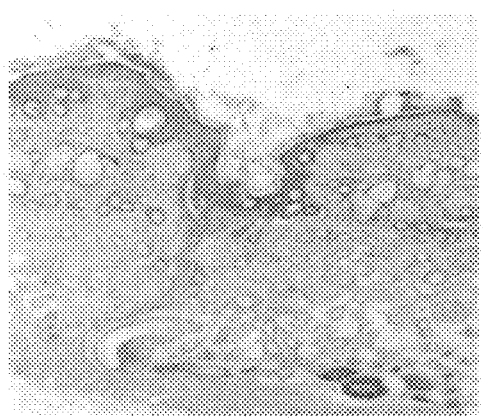
103
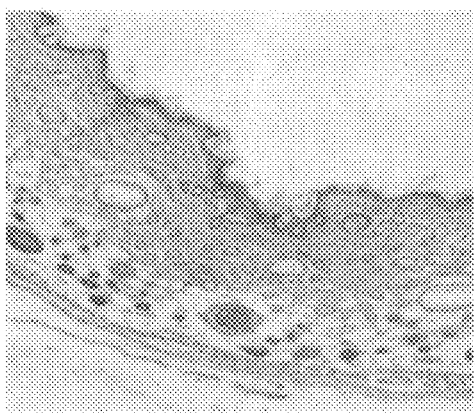
104
Fig: 4

COMPOSITION OBTAINABLE BY PASSING SINGLET OXYGEN THROUGH EXTRA VIRGIN OLIVE OIL

FIELD OF THE INVENTION

The present invention relates to a novel composition and methods of preparation thereof. More specifically, the compositions are useful as personal care products, as wound healing compositions, as a disinfectant and also for nosocomial infections.

BACKGROUND OF THE INVENTION

People often use the term "personal care products" to refer to a wide variety of items that we commonly find in the health and beauty sections of drug and department stores. The term "personal care product," however, is not defined by law. Under the law, some of the products commonly referred to as "personal care products" are cosmetics. These include, for example, skin moisturizers, perfumes, lipsticks, fingernail polishes, eye and facial makeup preparations, shampoos, permanent waves, hair colors, toothpastes, and deodorants. Some, however, are regulated as drugs. Among these are skin protectants (such as lip balms and diaper ointments), mouthwashes marketed with therapeutic claims, antiperspirants, and treatments for dandruff or acne.

Some "personal care products" meet the definitions of both cosmetics and drugs. This may happen when a product has two intended uses. For example, a shampoo is a cosmetic because its intended use is to cleanse the hair. An antidandruff treatment is a drug because its intended use is to treat dandruff. Consequently, an antidandruff shampoo is both a cosmetic and a drug, because it is intended to cleanse the hair and treat dandruff. Among other cosmetic/drug combinations are toothpastes that contain fluoride, deodorants that are also antiperspirants, and moisturizers and makeup marketed with sun-protection claims. Such products must comply with the requirements for both cosmetics and drugs.

Generally, drugs must either receive premarket approval by FDA or conform to final regulations specifying conditions whereby they are generally recognized as safe and effective, and not misbranded. Cosmetic products and ingredients are not subject to FDA premarket approval authority, with the exception of color additives. Cosmetic firms are responsible for substantiating the safety of their products and ingredients before marketing.

In addition, some "personal care products" may belong to other regulatory categories, including medical devices (such as certain hair removal and microdermabrasion devices), dietary supplements (such as vitamin or mineral tablets or capsules), or other consumer products (such as manicure sets).

Acne is a skin disorder resulting from the action of hormones and other substances on the skin's oil glands (sebaceous glands) and hair follicles affects about 85% of people to some degree in their adolescent lives. In severe cases, it can cause physical and/or emotional scarring as well.

The wound healing composition is topically applied to skin wounds, covering the outer surface of the wound. The heat shock protein acts by promoting migration of both human epidermal keratinocyte and dermal fibroblasts to the wound in order to close, heal, and remodel the wound by promoting both epidermal and dermal cell migration.

Dry skin is a problem in varying degree to most humans. This condition is particularly evident in winter. Personal care products such as skin creams/lotions, shampoos/conditioners, toilette bars/shower gels and antiperspirant/deodorants are normally formulated with at least one material to address dry skin. Symptoms such as itching flaking and a visually displeasing dermal appearance can all to some extend are modulated.

There are three classes of materials employed against the problem. Occlusives such as petrolatum or silicone oils serve to inhibit loss of natural moisture. They form a barrier between the epidermis and the environment. Another approach is the use of keratolytic agents to enhance rate of dermal exfoliation. Alpha-hydroxy acids are the most common agents for achieving exfoliation.

A third approach to dry skin is topical application of humectants. Hydroxylated monomeric and polymeric organic substances are generally used for this purpose. Glycerin known also as glycerol is one of the most effective humectants.

There are several shortcomings in the performance of known humectants. Even the best such as glycerin requires to be formulated at relatively high levels to achieve good moisturization.

Secondly, known humectants perform well in high relative humidity environments; however, hardly any of these substances provide effectiveness at low relative humidity (i.e. It is quite evident that a real need exists for an improved moisturization technology.

Accordingly, the present invention seeks to identify the composition, for application in personal care products.

Wound is a loss of tissue continuity caused by injury or any other source. Wound can occur in almost all part of the body and will be perfectly healed physiologically.

The wound healing processes occur in a few steps:
1. Hemostatic
2. Inflammation
3. Proliferation (Fibroplasia)
4. Maturation and Re-modelling.

In general, all kind of wounds will undertake these processes. Some factors may interfere in speeding up and helping the wound healing, either assisting by the application of any medical substances or none.

Accordingly, the present invention seeks to identify the composition for application in wound healing.

Nosocomial infections are tough tissues. Organisms causing nosocomial infections are usually opportunistic pathogens. The common bacteria causing nosocomial infections include Methicillin Resistant *Staph aureus* (MRSA; *E-coli* ESBL (Extended spectrum Beta-Lactamases); *K. Pneumoniae* ESBL (Extended Spectrum Beta-Lactamases); CRE (Carbapenem Resistant Enterobacteriaceae) and KPC (*Klebsiella pneumonia* carapenemases) and *Candida* Fungi.

Bacteria causing nosocomial infections may exist in stethoscopes, ananmesis papers, tourniquets, grooves, syringe needles, respirators, humidifiers, furniture, floors, vents, monitors, water, soil, food (fruits, vegetables), dirt in drainage, human body such as skin, armpits, mucosa!, oral cavity, upper respiratory tract, nasal cavity, gastrointestinal tract, etc. For example, nosocomial infections occur in an intensive care unit since patients in the intensive care unit have weak immunity and have invasive therapies such as being cannulated.

Antibiotics are general therapeutic agents for treating bacterial infections. However, when antibiotics are overused, bacteria will be selected to have resistance to the antibiotics. In current nosocomial infections, there are more and more bacteria having resistance to antibiotics, and patients infected by these bacteria have to be treated with expensive and novel antibiotics. Further, if the antibiotic resistance keeps developed, there will be no effective antibiotic for therapy. Hence, it is necessary to develop a method and/or a composition for reducing and/or preventing nosocomial infections.

As per the World Health Organization (WHO), a nosocomial infection—also called "hospital acquired infection" can be defined as: An infection acquired in hospital by a patient who was admitted for a reason other than that infection An infection occurring in a patient in a hospital or other health care facility in whom the infection was not present or incubating at the time of admission. This includes infections acquired in the hospital but appearing after discharge, and also occupational infections among staff of the facility.

Nosocomial infections occur worldwide and affect both developed and resource-poor countries. Infections acquired in health care settings are among the major causes of death and increased morbidity among hospitalized patients. They are a significant burden both for the patient and for public health. A prevalence survey conducted under the auspices of WHO in 55 hospitals of 14 countries representing 4 WHO Regions (Europe, Eastern Mediterranean, South-East Asia and Western Pacific) showed an average of 8.7% of hospital patients had nosocomial infections. At any time, over 1.4 million people worldwide suffer from infectious complications acquired in hospital. The highest frequencies of nosocomial infections were reported from hospitals in the Eastern Mediterranean and South-East Asia Regions (11.8 and 10.0% respectively), with a prevalence of 7.7 and 9.0% respectively in the European and Western Pacific Regions.

The most frequent nosocomial infections are infections of surgical wounds, urinary tract infections and lower respiratory tract infections. The WHO study, and others, has also shown that the highest prevalence of nosocomial infections occurs in intensive care units and in acute surgical and orthopedic wards. Infection rates are higher among patients with increased susceptibility because of old age, underlying disease, or chemotherapy.

Hospital-acquired infections add to functional disability and emotional stress of the patient and may, in some cases, lead to disabling conditions that reduce the quality of life. Nosocomial infections are also one of the leading causes of death. The economic costs are considerable. The increased length of stay for infected patients is the greatest contributor to cost. One study showed that the overall increase in the duration of hospitalization for patients with surgical wound infections was 8.2 days, ranging from 3 days for gynecology to 9.9 for general surgery and 19.8 for orthopedic surgery. Prolonged stay not only increases direct costs to patients or payers but also indirect costs due to lost work. The increased use of drugs, the need for isolation, and the use of additional laboratory and other diagnostic studies also contribute to costs. Hospital-acquired infections add to the imbalance between resource allocation for primary and secondary health care by diverting scarce funds to the management of potentially preventable condition.

The advancing age of patients admitted to health care settings, the greater prevalence of chronic diseases among admitted patients, and the increased use of diagnostic and therapeutic procedures which affect the host defenses will provide continuing pressure on nosocomial infections in the future. Organisms causing nosocomial infections can be transmitted to the community through discharged patients, staff, and visitors. If organisms are multi resistant, they may cause significant disease in the community.

Bacteriology of Commonly Isolated Nosocomial Pathogens

A multicenter study was conducted in Japan to isolate bacteria from surgical infections during 2011-2012. About 785 strains including 31 of *Candida* spp. were isolated from 204 out of 259 surgical patients. About 523 strains were isolated from primary infections and 231 from surgical site infection. From primary infections, anaerobic Gram-negative bacteria were prevalent. *Enterococcus* spp. was the highest among Grampositive aerobic bacteria followed by *Streptococcus* and *Staphylococcus* spp. *E. coli* was the predominant form among the Gram-negative aerobic bacteria followed by *K. pneumonia*, *P. aeruginosa* and *Enterobacter cloacae*.

*S. aureus*: Out of many species of *Staphylococcus* genus, *S. aureus* is considered one of the most important pathogens, responsible for nosocomial infections. It is Gram-positive cocci, non-spore forming, catalase- and coagulase-positive, immotile, facultatively anaerobe. It is not only a disease-causing organism but also plays its role as commensal. It mainly colonizes in nasal passages. About 20% individuals have persistent colonization of *S. aureus*, whereas 30% are intermittent. Hospitalized patients with decreased immunity and immune competent people in community are more prone to *S. aureus* infections. *S. aureus* infects not only the superficial but also the deep tissues and local abscess lesion. Toxin-mediated diseases of *S. aureus* include food poisoning, due to ingestion of enterotoxins, while toxic shock syndrome toxin 1 is responsible for toxic shock syndrome and exfoliative toxins cause staphylococcal scalded skin syndrome. Virulence mechanisms of *S. aureus* include toxins, enzymes and immune modulators.

*E. coli*: *E. coli* is an emerging nosocomial pathogen causing problems in health care settings. *E. coli* is Gram-negative and oxidase-negative facultative anaerobe bacteria. It can colonize in gastrointestinal tract of human beings and other animals. *E. coli* is responsible for a number of diseases including UTI, septicemia, pneumonia, neonatal meningitis, peritonitis and gastroenteritis. Virulence factors meant for its pathogenicity are endotoxins, capsule, adhesions and type 3 secretion systems. Specialized virulence factors are seen in case of UTI and gastroenteritis.

Vancomycin-resistant emerococci: Enterococci are the second leading cause of hospital acquired infections worldwide and the main leading cause in United States contributing 20%-30% of infections. These are facultative anaerobic Gram-positive enteric microbes. They are a part of normal microbiota in female genital tract and gastrointestinal tract as well. Enterococci are involved in the blood-borne infections; UTI and wound infections consort to surgical procedures. Virulence factors include extracellular surface proteins, cytolysin, adhesions, hemolysins, gelatinase, extra cellular superoxide and aggregation substances.

*K. pneumonia*: Three to seven percent of hospital-acquired bacterial infections are related to *K. pneumonia*, which is the eighth significant pathogen in healthcare settings. It is a Gram-positive *bacillus* and an opportunistic bacterium, which is a part of Enterobacteriaceae family. It usually colonizes gastrointestinal tract, pharynx and skin. It gets involved in diseases such as neonatal septicaemia, pneumonia, wound infections and septicemia. Its virulence factors include endotoxins, cell wall receptors and capsular polysaccharide.

*P. aeruginosa*: *P. aeruginosa* contributes to 11% of all nosocomial infections, which result in high mortality and morbidity rates. It is non-fermenter Gram-negative organism causing diseases especially among immune-compromised people. The sites of colonization are kidney, urinary tract and upper respiratory tract. It is a cause of surgical and wound infections, UTI, pneumonia, cystic fibrosis and bacteremia. Some of important virulence factors are adhesions, hemolysins, exotoxins, proteases and siderophores.

*Clostridium difficile* (*C. difficile*): *C. difficile* is an important nosocomial pathogen which mainly causes diarrhea. Several cases of *C. difficile* are reported in Europe, U.S. and Canada. It is a Gram-positive *bacillus*. It is anaerobic and spore-forming bacteria. It usually colonizes in intestinal tract and serves as part of normal microbiota. Diseases caused by toxins produced by *C. difficile* are colitis and it is responsible for 15%-25% cases of diarrhea. Major virulence factors for *C. difficile* are toxins, fimbriae, capsule and hydrolytic enzymes.

Accordingly, the present invention seeks to identify the composition for application to prevent nosocomial infection.

SUMMARY OF THE INVENTION

In general, the present invention relates to a novel composition and methods of preparation thereof. More specifically, the compositions are useful as personal care products, as wound healing compositions, as a disinfectant and also for nosocomial infections.

Accordingly, in a first aspect, the invention provides composition presented and defined by the components Methyl pelargonate, Methyl caprate, Methyl azelaaldehydate, Dimethyl suberate, Methyl 6,6,6-trimethoxy hexanoate, Dimethyl azelate, Methyl 6,6 dimethoxy octanoate, Methyl myristate, Dimethyl undecanediote, Methyl palmitate, Methyl linoleate, Methyl oleate, Methyl 8-octadecenoate, Methyl stearate, Methyl 2-octyl cyclopropaneoctanoate, Methyl 11-eicosenoate, Methyl eicosanoate, and Methyl docosanoate.

In another embodiment, the composition and pharmaceutically acceptable excipients are useful for personal care products.

In another embodiment, the composition and pharmaceutically acceptable excipients are being in solid, liquid and semi-solid form.

In another embodiment, the composition and pharmaceutically acceptable excipients can be used in form of form of cream, suppository, soap, body scrub, body oil, body wash, shampoo, hair conditioners, moisturizer, body oil, balm, baby products and solution.

In another embodiment, the composition and pharmaceutically acceptable excipients are useful in the treatment of acne, dandruff and dry skin.

In another embodiment, the composition and pharmaceutically acceptable excipients are useful for wound healing.

In another embodiment, the composition and pharmaceutically acceptable excipients are useful for nosocomial infection.

In another embodiment, the composition and pharmaceutically acceptable excipients are as a disinfectant.

BRIEF DESCRIPTION OF THE FIGURES

FIG. 1: Preparation of Incision to dressing.
FIG. 2: Application process of the drug test.
FIG. 3: Macroscopical results of the wound after 7 days.
FIG. 4: Microscopical results of the wound after 7 days.

DETAILED DESCRIPTION OF THE INVENTION

While the invention is susceptible to various modifications and/or alternative processes and/or compositions, specific embodiment thereof has been shown by way of example in the drawings, graphs and tables and will be described in detail below. It should be understood, however that it is not intended to limit the invention to the particular processes and/or compositions disclosed, but on the contrary, the invention is to cover all modifications, equivalents, and alternative falling within the spirit and the scope of the invention as defined by the appended claims. Before the present methods and the products are described, it is to be understood that this invention is not limited to particular method, product and experimental conditions described; as such methods and conditions may vary. It is also to be understood that the terminology used herein is for purposes of describing particular embodiments only, and is not intended to be limiting.

The tables, figures and protocols have been represented where appropriate by conventional representations in the drawings, showing only those specific details that are pertinent to understanding the embodiments of the present invention so as not to obscure the disclosure with details that will be readily apparent to those of ordinary skill in the art having benefit of the description herein.

The following description is of exemplary embodiments only and is not intended to limit the scope, applicability or configuration of the invention in any way. Rather, the following description provides a convenient illustration for implementing exemplary embodiments of the invention. Various changes to the described embodiments may be made in the function and arrangement of the elements described without departing from the scope of the invention.

The terms "comprises", "comprising", or any other variations thereof, are intended to cover a non-exclusive inclusion, such that one or more processes or composition/s or systems or methods proceeded by "comprises . . . a" does not, without more constraints, preclude the existence of other processes, sub-processes, composition, sub-compositions, minor or major compositions or other elements or other structures or additional processes or compositions or additional elements or additional features or additional characteristics or additional attributes.

The terms, "alone or in combination" or any other variations thereof, are intended to described and/or cover a non-exclusive inclusion, wherein the molecules or the oligonucleotides exist individually or together with any one or all of the other oligonucleotides.

Definitions

In this specification and in the claims that follow, reference will be made to a number of terms that shall be defined to have the following meanings:

It must be noted that, as used in the specification/description and the appended claims and examples, the singular forms "a", "an" and "the" may include plural referents unless the context clearly dictates otherwise.

An aspect of the present invention relates to a composition comprising methyl pelargonate, methyl caprate, methyl azelaaldehydate, dimethyl suberate, methyl 6,6,6-trimethoxy hexanoate, dimethyl azelate, methyl 6,6 dimethoxy octanoate, methyl myristate, dimethyl undecanediote, methyl palmitate, methyl linoleate, methyl oleate, methyl 8-octadecenoate, methyl stearate, methyl 2-octyl cyclopropaneoctanoate, methyl 11-eicosenoate, methyl eicosanoate, and methyl docosanoate.

In yet another aspect of the present invention, it relates to a composition comprising methyl pelargonate, methyl caprate, methyl azelaaldehydate, dimethyl suberate, methyl 6,6,6-trimethoxy hexanoate, dimethyl azelate, methyl 6,6 dimethoxyoctanoate, methyl myristate, dimethyl undecanediote, methyl palmitate, methyl linoleate, methyl oleate, methyl 8-octadecenoate, methyl stearate, methyl 2-octylcyclopropaneoctanoate, methyl 11-eicosenoate, methyl eicosanoate, and methyl docosanoate obtained by passing singlet oxygen through extra virgin olive oil.

An aspect of the present invention relates to a personal care product comprising the composition and a pharmaceutically acceptable excipient useful for personal care products.

An another aspect of the present invention relates to a product, wherein the personal care products are in the form of solid, liquid or semi-solid.

An another aspect of the present invention relates to personal care products, wherein the personal care products are in the form of cream, suppository, soap, body scrub, body oil, body wash, shampoo, hair conditioners, moisturizer, body oil, balm, baby products or solution.

Another aspect of the present invention relates to personal care products which are as and when used in the treatment of acne, dandruff and dry skin.

Another aspect of the present invention relates to composition for use is wound healing, nosocomial infection or disinfectant.

Another aspect of the present invention relates to a process for preparing a composition comprising methyl pelargonate, methyl caprate, methyl azelaaldehydate, dimethyl suberate, methyl 6,6,6-trimethoxy hexanoate, dimethyl azelate, methyl 6,6 dimethoxyoctanoate, methyl myristate, dimethyl undecanediote, methyl palmitate, methyl linoleate, methyl oleate, methyl 8-octadecenoate, methyl stearate, methyl 2-octylcyclopropaneoctanoate, methyl 11-eicosenoate, methyl eicosanoate, and methyl docosanoate, the process comprising the steps of:
  (a) preparing singlet oxygen,
  (b) passing the singlet oxygen through extra virgin olive oil, and
  (c) obtaining the composition comprising methyl pelargonate, methyl caprate, methyl azelaaldehydate, dimethyl suberate, methyl 6,6,6-trimethoxy hexanoate, dimethyl azelate, methyl 6,6 dimethoxyoctanoate, methyl myristate, dimethyl undecanediote, methyl palmitate, methyl linoleate, methyl oleate, methyl 8-octadecenoate, methyl stearate, methyl 2-octylcyclopropaneoctanoate, methyl 11-eicosenoate, methyl eicosanoate, and methyl docosanoate.

Another aspect of the present invention relates to a process wherein the singlet oxygen is passed through the extra virgin olive oil for a period of 325 to 385 hours.

Another aspect of the present invention relates to a process wherein the singlet oxygen is passed through the extra virgin olive oil for a period of about 360 hours.

In another aspect of the present invention, the wound may be caused by injury or any other source.

In another aspect of the present invention, the composition of the present invention results in perfect epithelialization, sufficient fibroplasia, and a lot of vascularization and no scars of the wound.

| No. | Real Time | Name | Structure | Proportion of all Ester in lipid acid (%) |
|---|---|---|---|---|
| 1 | 1.86 | Methyl Pelargonate $C_{10}H_{20}O_2$ | 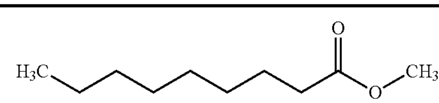 | 11.9 |
| 2 | 2.15 | Metyl Caprate $C_{11}H_{22}O_2$ | 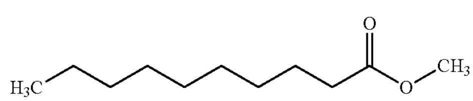 | 0.2 |
| 3 | 2.67 | Methyl Azelaaldehydate $C_{10}H_{18}O_3$ | 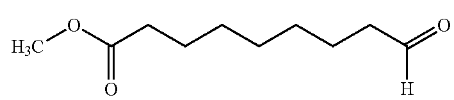 | 0.7 |
| 4 | 2.72 | Dimethyl Suberate $C_{10}H_{18}O_4$ | 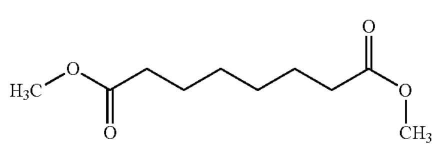 | 0.3 |
| 5 | 3.05 | Methyl 6,6,6-Trimethoxy Hexanoate $C_{11}H_{22}O_4$ | 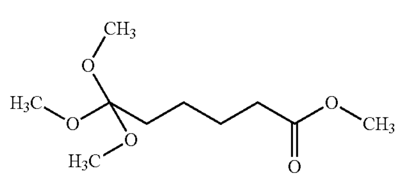 | 0.2 |
| 6 | 3.45 | Dimethyl Azelate $C_{11}H_{20}O_4$ | 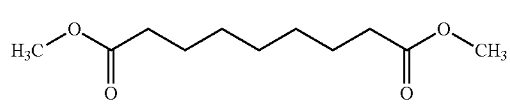 | 8.9 |

-continued
| No. | Real Time | Name | Structure | Proportion of all Ester in lipid acid (%) |
|---|---|---|---|---|
| 7 | 3.91 | Methyl 6,6 Dimethoxy Octanoate | 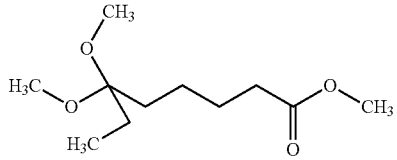 | 4.5 |
| 8 | 5.51 | Methyl Myristate $C_{15}H_{30}O_2$ | 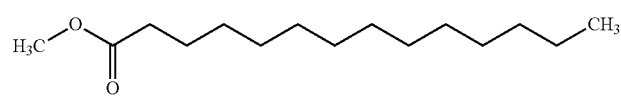 [SMILES: CCCCCCCCCCCCCC(=O)OC] | 0.1 |
| 9 | 5.89 | Dimethyl Un-decanediote $C_{12}H_{24}O_2$ | 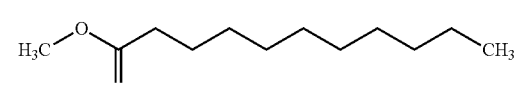 | 0.4 |
| 10 | 10.02 | Methyl Palmitate $C_{17}H_{34}O_2$ | 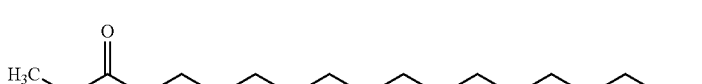 | 16.4 |
| 11 | 15.19 | Methyl Linoleate $C_9H_{34}O_2$ | 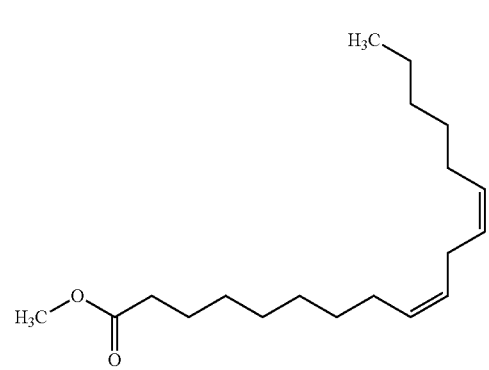 [SMILES: CCCCC/C=C\C/C=C\CCCCCCCC(=O)OC] | 3.1 |
| 12 | 15.43 | Methyl Oleate $C_{19}H_{36}O_2$ | 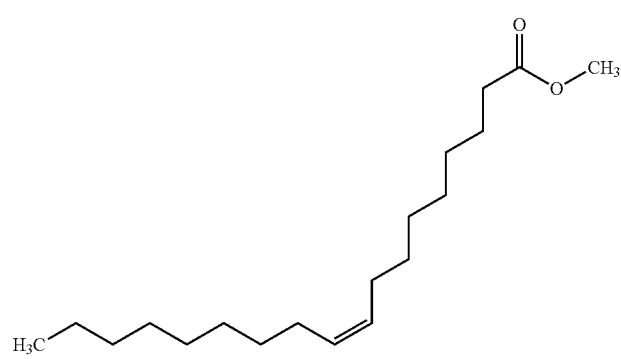 [SMILES: CCCCCCCC/C=C\CCCCCCCC(=O)OC] | 21.7 |
| 13 | 15.54 | Metil 8-Octadecenoate $C_{19}H_{36}O_2$ | 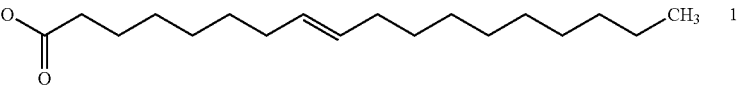 | 1 |
| 14 | 16.15 | Methyl Stearate $C_{19}H_{38}O_2$ | 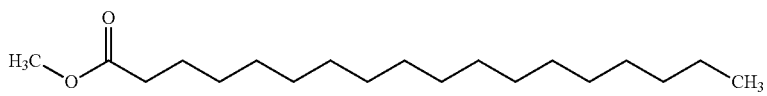 [SMILES: CCCCCCCCCCCCCCCCCC(=O)OC] | 27.8 |
| 15 | 19.61 | Methyl 2-OctylCyclo-propane-octanoate $C_{20}H_{38}O_2$ | 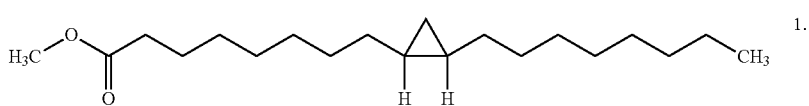 | 1.1 |

-continued

| No. | Real Time | Name | Structure | Proportion of all Ester in lipid acid (%) |
|---|---|---|---|---|
| 16 | 19.98 | Methyl 11-Eicosenoate $C_{21}H_{40}O_2$ | 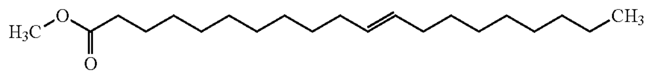 [SMILES: CCCCCCCC/C=C/CCCCCCCCCC(=O)OC] | 0.3 |
| 17 | 20.54 | Methyl Eicosanoate $C_{21}H_{42}O_2$ | 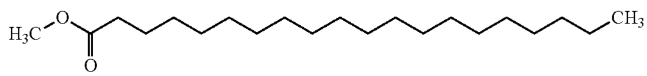 [SMILES: CCCCCCCCCCCCCCCCCCCC(=O)OC] | 1 |
| 18 | 24.20 | Methyl Docosanoate $C_{23}H_{46}O_2$ | 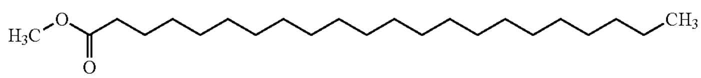 [SMILES: CCCCCCCCCCCCCCCCCCCCCC(=O)OC] | 0.5 |

EXAMPLES

The following description is of exemplary embodiments only and is not intended to limit the scope, applicability or configuration to the invention in any way. Rather, the following description provides a convenient illustration for implementing exemplary embodiments of the invention various changes to the described embodiments may be made in the functions and arrangement of the elements described without departing from the scope of the invention.

Example 1: Analysis Study Gas Chromatography, Free Fatty Acid, Acid, Iodine, Saponification, and Peroxide Value Research Protocol: Analysis Study Gas Chromatography, Free fatty Acid, Acid, Iodine, Saponification, dan Peroxide value on the composition
Tested Parameters: Oleic Acid, Acid value, Iodine Value, Saponification Value and Peroxide value
Result

| Parameter | Result | Method |
|---|---|---|
| Free fatty acid as Oleic Acid | [19.84 ± 0.3] % | Titration |
| Acid Value | [45.17 ± 1.1] | Titration |
| Iodine Value | [7.4 ± 0.8] | Volumetric |
| Saponification Value | [247 ± 1.5] | Volumetric |
| Peroxide Value | [745.4 ± 1.4] | Titration |

II. Lipid Gas Chromatography Profile
Conclusion

The laboratory tests consisting of Oleic Acid, Acid value, Iodine Value, Saponification Value and Peroxide value, have been performed. As the result of the GC test on, lipid profiles are indicated in the proportion of ester lipid acid (>10%): Methyl Pelargonate (11.9), Methyl Palmitate (16.4), Methyl Oleate (21.7) and Methyl Stearate (27.8).

Example 2: Effectivity Study on Microbes which Cause Nosocomial Infection

Backgrounds: Nosocomial infection may occur on patient or medical-staff in hospitals. It is epidemically occurred in developing-countries in Asia, Africa, and South-America (10-40%), but rarely found in developed-countries in North-America, Europe (1%). In general, 10% of the infections are found in patients who are treated at hospital. Mortality may increase on patients who have ever received surgery, get immunocompromised, or have been treated in the hospital for a long time.

The infection can get worse when a patient is contaminated by the germs found in hospital, known as Multi Drug Resistance Organisms (MDROs). The types of MDRO usually found at hospital are:
1. Methicillin Resistant *Staph aureus* (MRSA)
2. *E-coli* ESBL (Extended Spectrum Beta-Lactamases)
3. *K. Pneumoniae* ESBL (Extended Spectrum Beta-Lactamases)
4. CRE (Carbapenem Resistant Enterobacteriaceae) a.1 KPC (*Klebsiella pneumoniae* carbapenemases)
5. *Candida* fungi Those pathogens are commonly found from patient's clinical isolate, that the scope for the therapy becomes tight and limited, and an antibiotics-injection is required.
Material
1. Composition in liquid form
2. Liquid bacterial growth medium (Mueller Hinton Broth)
3. Bacteria's Clinical Isolate
  1. Methicillin Resistant *Staph aureus* (MRSA)
  2. *E coli* ESBL (Extended Spectrum Beta-Lactamases)
  3. K. *Pneumoniae* ESBL (Extended Spectrum Beta-Lactamases)
  4. CRE (Carbapenem Resistant Enterobacteriaceae) a.1 KPC (*Klebsiella pneumoniae* carbapenemases) 5. *Candida* fungi
No Batch WIP 030616 (110 CPS)
No Batch 010616 (560 CPS)
No Batch 010616 (580 CPS)
Method
The method of dilution sensitivity test (Tube Test), following these steps:
1. 1 ml bacteria suspension is added to tube I, 1 ml with 100% concentration
2. 1 ml bacteria suspension is added to tube II, 1 ml with 50% concentration
3. 1 ml bacteria suspension is added to tube III, 1 ml with 25% concentration
4. 1 ml bacteria suspension is added to tube IV, 1 ml with 12.5% concentration
5. 1 ml bacteria suspension is added to tube V, 1 ml with 6.25% concentration
6. 1 ml bacteria suspension is added to tube VI, 1 ml with 3.125% concentration
7. Make 1 ml positive control solution and add 1 ml aquadest
8. Incubate at the incubator for 24 hours.

9. Observe the results by comparing with control solution, clearer tube indicates the minimum inhibitory concentration (MIC)
10. Do the streaking for two tubes before and after MIC on a plate, or pour it on the plate to see minimum bactericidal concentration (MBC). Incubate for 24 hours.

Results
1. MRSA Bacteria

TABLE 1a

Using WIP 030616 (110CPS)

| Strain MRSA | 100% | 50% | 25% | 12.5% | 6.25% | 3.125% |
|---|---|---|---|---|---|---|
| 6 | + | + | + | + | + | + |
| 10 | + | + | + | + | + | + |
| 11 | + | + | + | + | + | + |
| 12 | + | + | + | + | + | + |
| 13 | + | + | + | + | + | + |

Explanation: +cloudy pathogen's growth on the plate is visible

TABLE 1b

Using 010616 (560 CPS)

| Strain MRSA | 100% | 50% | 25% | 12.5% | 6.25% | 3.125% |
|---|---|---|---|---|---|---|
| 6 | 0 | 0 | + | + | + | + |
| 10 | 0 | 0 | + | + | + | + |
| 11 | 0 | 0 | + | + | + | + |
| 12 | 0 | 0 | + | + | + | + |
| 13 | 0 | 0 | + | + | + | + |

Explanation: 0 Absence of bacteria's growth
+min minimum pathogen's growth is visible
+cloudy and there are pathogen's growth on the plate is visible 2. Other MDROs Bacteria

TABLE 2 using 010616 (580 CPS)

| Strain | 100% | 50% | 25% | 12.5% | 6.25% | 3.125% |
|---|---|---|---|---|---|---|
| E coli ESBL | 0 | 0 | + | + | + | + |
| K pneu ESBL | 0 | 0 | + | + | + | + |
| KPC | 0 | 0 | + | + | + | + |

Explanation: 0 Absence of bacteria's growth
+min minimum pathogen's growth is visible
+cloudy and there are pathogen's growth on the plate is visible 3. *Candida* Fungi

TABLE 3

Using 010616 (580 CPS)

| Strain Candida | 100% | 50% | 25% | 12.5% | 6.25% | 3.125% |
|---|---|---|---|---|---|---|
| Albicans | 0 | 0 | + | + | + | + |
| Kruseii | 0 | 0 | 0 | 0 | + | + |
| tropicalis | 0 | 0 | +min | + | + | + |
| Glabrata | 0 | 0 | 0 | + | + | + |

Explanation: 0 Absence of bacterias growth
+min t minimum bacteria growth is exist
+cloudy and there are pathogen's growth on the plate is visible Conclusion: After doing sensitivity test on microbes that cause nosocomial infection, the conclusions are:
1. Other MDRO (ESBL and KPC) can be inhibited and terminated at 50% concentration
2. *Candida* fungi can be inhibited and terminated at 50% concentration Example 3: Acute Toxicity Study on the Incised Wound Healing *Rattus Norvegicus*: In Vivo Research on Animals Research Protocol: Acute Toxicity Study on the Incised Wound healing *Rattus Norvegicus* In Vivo research on animals Background: Wound is a loss of tissue continuity caused by injury or any other source. Wound can occur in almost all part of the body and will be perfectly healed physiologically. The wound Healing Processes occur in a few steps:
1. Hemostatic
2. Inflammation
3. Proliferation (Fibroplasia)
4. Maturation and Remodelling.

In general, all kind of wounds will undertake these processes. Some factors may interfere in speeding up and helping the wound healing, either assisting by the application of any medical substances or none.

Material
1. Composition comprising a mixture composed of methyl pelargonate, methyl caprate, methyl azelaaldehydate, dimethyl suberate, methyl 6,6,6-trimethoxy hexanoate, dimethyl azelate, methyl 6,6 dimethoxyoctanoate, methyl myristate, dimethyl undecanediote, methyl palmitate, methyl linoleate, methyl oleate, methyl 8-octadecenoate, methyl stearate, methyl 2-octylcyclopropaneoctanoate, methyl 11-eicosenoate, methyl eicosanoate, and methyl docosanoate.
2. Vaseline
3. Sibro (from Mebo)
4. Gentamicin ointment (generic)

Methods
1. Preparation of animals:
1. Inject the animals with anesthesia drug containing ketamine hydrochloride, 0.1-0.2 ml as illustrated in 101 of FIG. 1.
2. Place them back into the cage while waiting them fully unconscious as the effect of the drug.
3. Shave the back hair of the animals with razor blade.
4. Give antiseptics, i.e. povidone iodine and alcohol. Wait for three minutes as illustrated in 102 of FIG. 1.
5. Make a 2-cm long incision on the animal's back as illustrated in 103 of FIG. 1. Should any bleeding occurred, wipe with cotton.
6. Apply cotton bud ton the incision spot.
7. Cover the spot with gauze bandage and stick it with plaster as illustrated in 104 of FIG. 1.
8. Place the animal back in to the cage.

2. Fixation Tissue Protocol
The skin organs from treatment and control group are taken after the incision, then put them to the bottles containing fixation solution, and give labels. The intensions of the fixation are:
1. To maintain cell structure and component.
2. To prevent autolysis on post mortem 3. To prevent decomposition and bacteria/fungi growth There are various solutions used for the fixation process, but this research used neutral buffer formalin, which contains:

Formaldehyde 40%: 100 cc
Aquadestilata: 900 cc
Sodium hydrogen posphate monobasic ($NaH_2PO_4$): 4 gr
Sodium hydrogen posphate dibasic ($Na_2HPO_4$): 6.5 gr
Minimum time of fixation is 12-18 hour before the next process.

3. Tissue Processing Protocol/Paraffin Block

The tissue's processing is started after the fixation completed. The steps of this process are dehydration, clearing, and impregnation/embedding. Dehydration is taken by dehydrating the tissue using ethanol in the gradually increased concentrate until the absolute concentrate is reached. Afterward, do the clearing by place the tissue into xylol. Then, do the impregnation/embedding by using paraffin. The detail of this process is as follows:

After the fixation is completed, the tissues are placed into the following solution, consecutively.

1. Alcohol 70%: -
2. Alcohol 80% 1 hour
3. Alcohol 95%: 2 hour
4. Alcohol 95%: 1 hour
5. Alcohol 100%: 1 hour
6. Alcohol 100%: 1 hour
7. Alcohol 100%: 1 hour
8. Xylol: 1 hour
9. Xylol: 1 hour
10. Xylol: 2 hour
11. Paraffin (56-58° C.): 2 hour
12. Paraffin (56-58° C.) 2 hour
13. Paraffin (56-58° C.) 2 hour After this process, block the tissue into paraffin with this steps; first, prepare paraffin block printer, place it to a flat surface, pour liquid paraffin (56-60° C.) into the printer and take the tissue from impregnation process, put it into the printer that contain liquid paraffin, give label, wait for a few minutes until the paraffin is frozen, then take it out from the printer. These steps called Embedding.

4. Tissue Slicing and Attaching Process on object glass Protocol.

The next process is to slice the tissue and attach it on object glass.

1. Tissue that already inside the paraffin block is sliced with microtome for 4 micron thick
2. Ribbon slice is taken into water bath which has temperature between 45-55° C., with object glass that has been applied with albumin glue.
3. The ribbon slice is attached into object glass and let it dry on room temperature
4. To make tissue attached into object glass, heat it into the oven at 56-58° C. for 3-4 hour,
5. Remove from the oven and live it in room temperature, then the tissue is ready to dye.

5. Hematoxilin Eosin Dyeing Protocol

The steps of HE dyeing method are:
Dip the object glass which contains tissue into solution:
1. Xylol 1,2,3
2. Absolute Alcohol 1×
3. Alcohol 96% 2×, wash under running water, if use zenker clip in to lugol for 1 minutes, iodine alcohol for 10-15 minutes, wash sodium thiosulfate (hypo), wash with water.
4. Harris hematoxilin 10-15 minutes
5. Wash under running water
6. Acid alcohol, 3-10 dip to suit the color.
7. Wash under running water
8. Ammoniac water 1-5 dips, check under microscope, the nucleus is blue
9. Wash under running water
10. Eosin 1-5 minutes
11. Alcohol 95 2×1-5 minutes
12. Absolute alcohol 2×1-5 minutes
13. Xylol 3×5 minutes
14. Mounting with entellan and cover glass 6. Observe Results 1. The animals were managed to survive after being applied the substances to their incised wound.
2. The wound of the animals were increasingly healed macroscopically
3. The wound of the animals were increasingly healed microscopically Results of the Research 1. The animals were manage to survive after being applied the substances to their incise wound This research use 24 Rats divided into 4 groups of treatment; they are Vaseline, Sibro, Gentamicin and Test. Composition. Each group has 6 rats.

On the second day, 1 rat died from Vaseline group.

TABLE 1

Animals that survived after being applied the substance on day −7

| Group | Amount of Rats | Dead Rats | Survival on day −7 |
|---|---|---|---|
| Vaselin | 6 | 1 | 5/6 |
| Sibro | 6 | 0 | 6/6 |
| Gentamisin | 6 | 0 | 6/6 |
| Test Composition | 6 | 0 | 6/6 |

2. The Wound of the Animals were Increasingly Healed Macroscopically

In this research, a 2-cm long incision was made on the animal's back using razor blade after they were anesthetized with ketamine injection on the tight. After then stopped the bleeding, applied Vaseline, Sibro, Gentamicin and Test Composition to each group.

Application of Vaseline (201), Sibro (202), Gentamicin (203) and Test Composition (204) are illustrated in FIG. 2.

TABLE 2

Incised wound macroscopic condition

| Group | Amount of Rats | Survival day −7 | Wound condition on day −7 |
|---|---|---|---|
| Vaselin | 6 | 5/6 | Closing |
| Sibro | 6 | 6/6 | Closing (with 1 granulation) |
| Gentamisin | 6 | 6/6 | Closing (with 1 granulation) |
| Test Composition | 6 | 6/6 | Closing (with 2 granulation) |

Macroscopic condition of the wound with Vaseline (301), Sibro (302), Gentamicin (303) and Test Composition (304) after 7 days are illustrated in FIG. 3.

3. The Wound of Animals were Increasingly Healed Microscopically

There are 4 parameters in observing incised wound microscopically, they are Epithelization, Fibroplasia, Neovascularization, and scar.

| Group | Epitheliazation | Fibroplasia | Neo vascularization | Scar |
|---|---|---|---|---|
| Vaselin | + | + | + | + |
| Sibro | + | ++ sufficient | + | + |
| Gentamisin | + | + | ++ | + |
| Test Composition | + | ++ sufficient | ++ | 0 |

Ket:
0 absence,
+ visible,
++ visible, a lot or thick

Microscopical results of the wound with Vaseline (401), Sibro (402), Gentamicin (403) and Test Composition (404) are illustrated in FIG. 4.

Conclusion

1. Based on this research, the applying of composition on animals was non-toxic on the animals, and they were managing to survive until day-7.
2. The applying of the composition had increasingly healed their wounds macroscopically on day 7.
3. The applying of the composition had increasingly healed their wounds microscopically, indicated by the perfect epithelization, sufficient fibroplasia, and a lot of vascularization so there are no scars on day 7.

Example 4

Effectivity Study on Infected Incised Wound of *Rattus Norvegicus* Experimental Research on Animal Testing
Background: Wound is a continuity loss of tissue as the result of an injury or any other cause.

Wound can occur in almost all part of the body and will be perfectly healed physiologically.
The wound healing processes occur in the following stages:
1. Hemostatic.
2. Intimation.
3. Proliferation (Fibroplasia).
4. Maturation and Remodelling.

When a wound got infected, it can affect a serious problem in the healing process.
The infection is usually caused by the microbes from patient's body or from the environment. Certain microbes that caused infection can be resistant on anti-microbes that called MDROs (Multiple Drugs Resistance Organisms). Here are the MDRO usually found at the hospital:
1. Methicillin Resistant *Staph aureus* (MRSA)
2. *E coli* ESBL (Extended Spectrum Beta-Lactamases)
3. *K. Pneumoniae* ESBL (Extended Spectrum Beta-Lactamases)
4. CRE (Carbapenem Resistant Enterobacteriaceae) a.1 KPC (*Klebsiella pneumoniae* carbapenemases)
5. *Candida* Fungus Those microbes are usually found from the patient's clinical isolates, so the therapy spectrum became more narrow and limited, and an antibiotic-injection is required.

Material

1. Composition comprising a mixture composed of methyl pelargonate, caprate, methyl azelaaldehydate, dimethyl suberate, methyl 6,6,6-trimethoxy hexanoate, dimethyl azelate, methyl 6,6 dimethoxyoctanoate, methyl myristate, dimethyl undecanediote, methyl palmitate, methyl linoleate, methyl oleate, methyl 8-octadecenoate, methyl stearate, methyl 2-octylcyclopropaneoctanoate, methyl 11-eicosenoate, methyl eicosanoate, and methyl docosanoate.
2. Bacteria's Growth Media solution (Mueller Hinton Broth)
3. Vaseline
4. Mupirocin (for MRSA)
5. Clinical isolate of bacteria, such as:
1. *Staphylococcus aureus*
2. *Staphylococcus epidermidis*
3. *Streptococcus pyogenes*
4. *Pseudomonas aeruginosa*
5. *Acinetobacter baumanii*
6. Methicillin Resistant *Staph aureus* (MRSA)
7. *E coli* ESBL (Extended Spectrum Beta-Lactamases)
8. *K. Pneumoniae* ESBL (Extended Spectrum Beta-Lactamases)
9. CRE (Carbapenem Resistant Enterobacteriaceae) a.1 KPC (*Klebsiella pneumoniae* carbapenemases)
10. *Candida* Fungus Method: Solution Preparation Protocol for Infected Incised Wound
Preparing the solution with these following steps:
1. Bacteria from the infected patient clinical isolate is planted on the media by streaking at for quadrant
2. The isolated bacteria in separated colonies are dissolved in the tube that contain pz liquid
3. In order to analyze the cloudness level of the solution on the tube, nephelometer is used to figure the cloudness level to 0.50 McFarland.
4. 0.5 McFarland is equal to 1.5×108 CFU bacteria.

Infected Incised Wound Preparation Protocol on Animals

1. Preparation of animals:
1. Inject the animals with anesthesia drug containing ketamine hydrochloride, 0.1-0.2 ml
2. Place them back into the cage while waiting them to be fully unconscious as the effect of the drug.
3. Shave the back hair of the animals with razor blade.
4. Give antiseptics, i.e. povidone iodine and alcohol. Wait for three minutes.
5. Make a 2-cm long incision on the animal's back. Should any bleeding occurred, wipe with cotton.
6. Swipe the incised spot with the bacteria solution using a cotton bud.
7. Cover the spot with gauze bandage and stick it with plaster.
8. Place the animal back in to the cage.
9. If there is any requirement for adding test material, the material should be shortly added up on the wound before it is bandaged.

Protocols for Making Histology Preparate and Dyeing Technique of Hematoxilin Eosin 1. Protocol for Fixation Tissue The skin organs from treatment and control group are taken after the incision then put them to the bottles containing fixation solution, and give labels. The intentions of the fixation are:
1. To maintain cell structure and component.
2. To prevent autolysis on post mortem
3. To prevent decomposition and bacteria/fungi growth
There are various solutions used for the fixation process, but this research used neutral buffer formalin, which contains:
Formaldehyde 40%: 100 cc
Aquadestilata: 900 cc
Sodium hydrogen posphate monobasic ($NaH_2PO_4$): 4 gr
Sodium hydrogen posphate dibasic ($Na_2HPO_4$): 6.5 gr
Minimum time of fixation is 12-18 hour before the next process.

2. Protocol for Tissue Processing/Paraffin Block

The tissue's processing is started after the fixation completed. The steps of this process are dehydration, clearing, and impregnation/embedding. Dehydration is taken by dehydrating the tissue using ethanol in the gradually increased concentrate until the absolute concentrate is reached. Afterward, do the clearing by place the tissue into xylol. Then, do the impregnation/embedding by using paraffin. The detail of this process is as follows:
After the fixation is completed, the tissues are placed into the following solution, consecutively.
1. Alcohol 70%: -
2. Alcohol 80%: 1 hour
3. Alcohol 95%: 2 hour
4. Alcohol 95%: 1 hour
5. Alcohol 100%: 1 hour
6. Alcohol 100%: 1 hour
7. Alcohol 100%: 1 hour
8. Xylol: 1 hour
9. Xylol: 1 hour
10. Xylol: 2 hour
11. Paraffin (56-58° C.): 2 hour
12. Paraffin (56-58° C.) 2 hour
13. Paraffin (56-58° C.) 2 hour
After this process, block the tissue into paraffin with this steps; first, prepare paraffin block printer, place it to a flat surface, pour liquid paraffin (56-60° C.) into the printer and take the tissue from impregnation process, put it into the printer that contain liquid paraffin, give label, wait for a few minutes until the paraffin is frozen, then take it out from the printer. This steps called Embedding.
3. Protocol for Tissue Slicing and Attaching Process on object glass.
The next process is to slice the tissue and attach it on object glass.
1. Tissue that already inside the paraffin block is sliced using microtome for 4 micron thick
2. Ribbon slice is taken into water bath which has temperature between 45-55° C., with object glass that have been applied with albumin glue.
3. The ribbon slice is attached into object glass and let it dry on room temperature
4. To make tissue attached into object glass, heat it into the oven at 56-58° C. for 3-4 hour,
5. Remove from the oven and leave it in room temperature, then the tissue is ready to dye.
4. Hematoxilin Eosin Dyeing Protocol
The steps of HE dyeing method are:
Dip the object glass which contains tissue into solution:
1. Xylol 1,2,3
2. Absolute Alcohol 1×
3. Alcohol 96% 2×, wash under running water, if use zenker dip in to lugol for 1 minutes, iodine alcohol for 10-15 minutes, wash sodium thiosulfate (hypo), wash with water.
4. Harris hematoxilin 10-15 minutes
5. Wash under running water
6. Acid alcohol, 3-10 dip to suit the color.
7. Wash under running water
8. Ammoniac water 1-5 dips, check under microscope, the nucleus is blue
9. Wash under running water
10. Eosin 1-5 minutes
11. Alcohol 95 2×1-5 minutes
12. Absolute alcohol 2×1-5 minutes
13. Xylol 3×5 minutes
14. Mounting with entellan and glass cover
Observation Results
4. The animals were managed to survive after being applied the substances to their incised wound.
5. The wound of the animals were increasingly healed macroscopically
6. The wound of the animals were increasingly healed microscopically
Result of the Research
4. Survival after adding another substances to their incise wounds
This research use more than 1-Rats divided into 3 groups which is nosocomial, MDRO, and fungus. Each group has sub group with 6 rats.
On the second day, 1 rat died from *Acinobacter bumanii*, and *Streptococcus pyogenes* group.

|  | Number of rats | Dead Rats | Survival |
|---|---|---|---|
| Group I Nosocomial (n = 60) | | | |
| *Staph aureus* + Vaseline | 6 | 0 | 6/6 |
| *Staph aureus* + Medcare | 6 | 0 | 6/6 |
| *Staph epidermidis* + Vaseline | 6 | 0 | 6/6 |
| *Staph epidermidis* + Medcare | 6 | 0 | 6/6 |
| *Streptococcus pyogenes* + Vaseline | 6 | 1 | 5/6 |
| *Streptococcus pyogenes* + Medcare | 6 | 0 | 6/6 |
| *Pseudomonas aeruginosa* + Vaseline | 6 | 0 | 6/6 |
| *Pseudomonas aeruginosa* + Medcare | 6 | 0 | 6/6 |
| *Acinetobacter baumanii* + Vaseline | 6 | 1 | 5/6 |
| *Acinetobacter baumanii* + Medcare | 6 | 0 | 6/6 |
| Group II MDRO (n = 72) | | | |
| MRSA 10 vaseline | 6 | 0 | 6 |
| MRSA10 mupirocine | 6 | 0 | 6 |
| MRSA 10 medcare | 6 | 0 | 6 |
| MRSA 6 mupirocine | 6 | 0 | 6 |
| MRSA 6 mupirocine | 6 | 0 | 6 |
| MRSA 6 medcare | 6 | 0 | 6 |
| E coli ESBL vaseline | 6 | 0 | 6 |
| E coli ESBL medcare | 6 | 0 | 6 |
| K pneumonia ESBL vaseline | 6 | 0 | 6 |
| K pneumonia ESBL medcare | 6 | 0 | 6 |
| KPC Vaseline | 6 | 0 | 6 |
| KPC medcare | 6 | 0 | 6 |
| Group III Fungi (n = 48) | | | |
| *Candida albican* Vaseline | 6 | 0 | 6 |
| *Candida albican* medcare | 6 | 0 | 6 |
| *Candida krusei* Vaseline | 6 | 0 | 6 |
| *Candida krusei* medcare | 6 | 0 | 6 |
| *Candida glabrata* Vaseline | 6 | 0 | 6 |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in responsiveness of the mammal being treated for any of the indications with the compounds of the invention indicated above. The specific pharmacological responses observed may vary according to and depending upon the particular active compounds selected or whether there are present pharmaceutical carriers, as well as the type of formulation and mode of administration employed, and such expected variations or differences in the res tills arc contemplated in accordance with the objects and practices of the present invention. It is intended, therefore, that the invention be defined by the scope of the claims which follow and that such claims be interpreted as broadly as is reasonable.

I claim:
1. A composition comprising methyl pelargonate, methyl caprate, methyl azelaaldehydate, dimethyl suberate, methyl

6,6,6-trimethoxy hexanoate, dimethyl azelate, methyl 6,6 dimethoxyoctanoate, methyl myristate, dimethyl undecanedioate, methyl palmitate, methyl linoleate, methyl oleate, methyl 8-octadecenoate, methyl stearate, methyl 2-octylcyclopropaneoctanoate, methyl 11-eicosenoate, methyl eicosanoate, and methyl docosanoate, wherein the composition is obtained by passing singlet oxygen through extra virgin olive oil for a period of 325 to 385 hours.

2. A personal care product comprising the composition as claimed in claim 1, and a pharmaceutically acceptable excipient.

3. The personal care product as claimed in claim 2 in the form of a solid, a liquid, or a semi-solid.

4. The personal care product as claimed in claim 3 in the form of a cream, a suppository, a soap, a body scrub, a body oil, a body wash, a shampoo, a hair conditioner, a moisturizer, a body oil, a balm, a baby product or a solution.

5. The personal care product as claimed in claim 4 for use in treatment of acne, dandruff and dry skin.

6. The composition as claimed in claim 1 for use in wound healing, nosocomial infection or disinfection.

7. A process for preparing a composition comprising methyl pelargonate, methyl caprate, methyl azelaaldehydate, dimethyl suberate, methyl 6,6,6-trimethoxy hexanoate, dimethyl azelate, methyl 6,6 dimethoxyoctanoate, methyl myristate, dimethyl undecanediote, methyl palmitate, methyl linoleate, methyl oleate, methyl 8-octadecenoate, methyl stearate, methyl 2-octyl cyclopropaneoctanoate, methyl 11-eicosenoate, methyl eicosanoate, and methyl docosanoate, the process comprising the steps of:
(a) preparing singlet oxygen;
(b) passing the singlet oxygen through extra virgin olive oil for a period of 325 to 385 hours; and
(c) obtaining the composition comprising methyl pelargonate, methyl caprate, methyl azelaaldehydate, dimethyl suberate, methyl 6,6,6-trimethoxy hexanoate, dimethyl azelate, methyl 6,6 dimethoxyoctanoate, methyl myristate, dimethyl undecanedioate, methyl palmitate, methyl linoleate, methyl oleate, methyl 8-octadecenoate, methyl stearate, methyl 2-octyl cyclopropaneoctanoate, methyl 11-eicosenoate, methyl eicosanoate, and methyl docosanoate.

\* \* \* \* \*